(12) United States Patent
Anderson

(10) Patent No.: US 12,232,746 B1
(45) Date of Patent: *Feb. 25, 2025

(54) SURGICAL SAW BLADE FOR WEDGE OSTEOTOMIES

(71) Applicant: CORTICAL EDGE ORTHOPEDICS LLC, Hayward, WI (US)

(72) Inventor: Keith Richard Anderson, Hayward, WI (US)

(73) Assignee: Cortical Edge Orthopedics LLC, Hayward, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/648,085

(22) Filed: Apr. 26, 2024

Related U.S. Application Data

(60) Division of application No. 17/873,956, filed on Jul. 26, 2022, now Pat. No. 11,998,219, which is a continuation of application No. 16/734,793, filed on Jan. 6, 2020, now Pat. No. 11,395,663, which is a continuation of application No. 14/605,634, filed on Jan. 26, 2015, now Pat. No. 10,524,803, which is a continuation of application No. 12/732,398, filed on Mar. 26, 2010, now Pat. No. 8,939,981.

(60) Provisional application No. 61/164,594, filed on Mar. 30, 2009.

(51) Int. Cl.
*A61B 17/14* (2006.01)
(52) U.S. Cl.
CPC ............ *A61B 17/142* (2016.11); *A61B 17/14* (2013.01)

(58) Field of Classification Search
CPC ..... A61B 17/14; A61B 17/142; A61B 17/144; A61B 17/147; A61B 17/149
See application file for complete search history.

(56) References Cited

U.S. PATENT DOCUMENTS

| | | | |
|---|---|---|---|
| 254,733 | A | 3/1882 | Valentine |
| 349,119 | A | 9/1886 | Phillips |
| 435,538 | A | 9/1890 | Fletcher |
| 1,507,264 | A | 9/1924 | Stevenson |
| D282,205 | S | 1/1986 | Davison et al. |
| 4,625,725 | A | 12/1986 | Davison et al. |
| 5,087,261 | A | 2/1992 | Ryd et al. |
| 5,342,365 | A | 8/1994 | Waldman |
| 5,441,501 | A | 8/1995 | Kenyon |
| 5,569,257 | A | 10/1996 | Arnegger et al. |
| 5,620,448 | A | 4/1997 | Puddu |
| 5,690,316 | A | 11/1997 | Madjarac |
| 5,749,875 | A | 5/1998 | Puddu |

(Continued)

OTHER PUBLICATIONS

Web pages displaying surgical saw blade images, available at http://vilex.com/vilex-surgical-products/power-equipment-and-accessories/hand-pieces-and-accessories (last visited Aug. 19, 2014).

*Primary Examiner* — Si Ming Ku
(74) *Attorney, Agent, or Firm* — Garvey, Smith & Nehrbass, Patent Attorneys, L.L.C.; Julia M. FitzPatrick; Gregory C. Smith

(57) ABSTRACT

A surgical blade having an attachment base positioned at a proximal end and a wedge-shaped blade. The wedge-shaped blade includes a cutting tip having a first plurality of cutting teeth, which define a cutting edge along the distal end for starting an osteotomy. The wedge-shaped blade includes a second plurality of teeth positioned along rows. Each row is positioned at offset planes from adjacent rows along the wedge-shaped blade.

18 Claims, 3 Drawing Sheets

(56) References Cited

U.S. PATENT DOCUMENTS

| | | | |
|---|---|---|---|
| 6,120,508 | A | 9/2000 | Grunig et al. |
| D612,050 | S | 3/2010 | Baynham |
| 8,939,981 | B1 | 1/2015 | Anderson |
| 10,524,803 | B1 | 1/2020 | Anderson |
| 11,395,663 | B2 | 7/2022 | Anderson |
| 11,998,219 | B2 | 6/2024 | Anderson |
| 2004/0098000 | A1* | 5/2004 | Kleinwaechter ...... B23D 61/123 D24/146 |
| 2004/0243136 | A1* | 12/2004 | Gupta ................... B23D 61/121 606/82 |
| 2005/0113840 | A1 | 5/2005 | Metzger et al. |
| 2007/0233131 | A1 | 10/2007 | Song et al. |
| 2009/0093815 | A1* | 4/2009 | Fletcher ................. B23D 51/10 606/82 |
| 2009/0312762 | A1 | 12/2009 | Boykin |

* cited by examiner

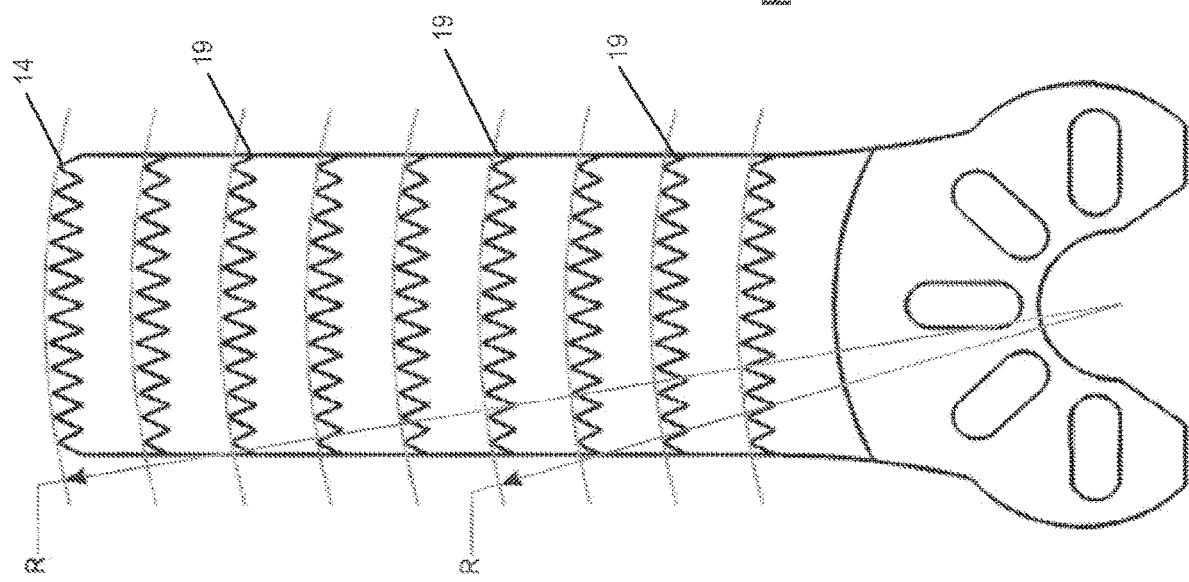

SURGICAL SAW BLADE FOR WEDGE OSTEOTOMIES

CROSS-REFERENCE TO RELATED APPLICATIONS

This application is a division of U.S. patent application Ser. No. 17/873,956, filed Jul. 26, 2022, which is a continuation application of U.S. patent application Ser. No. 16/734,793, filed Jan. 6, 2020 (issued as U.S. Pat. No. 11,395,663 on Jul. 26, 2022), which is a continuation application of U.S. patent application Ser. No. 14/605,634, filed Jan. 26, 2015 (issued as U.S. Pat. No. 10,524,803 on Jan. 7, 2020), which is a continuation of U.S. patent application Ser. No. 12/732,398, filed Mar. 26, 2010 (issued as U.S. Pat. No. 8,939,981 on Jan. 27, 2015), which claims the benefit of and/or priority to U.S. Provisional Patent Application Ser. No. 61/164,594, filed Mar. 30, 2009, each of which is hereby incorporated herein by reference in its entirety.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention generally relates to surgical devices. More particularly, the present invention relates to a surgical saw blade for wedge osteotomies.

2. General Background of the Invention

Current surgical saw blades make straight or crescentic shaped osteotomies. This causes the user to make multiple osteotomies to resect a wedge of bone. Creation of multiple osteotomies is time consuming, and can create inconsistent wedge sizes and planar inaccuracies.

As can be seen, there is a need for a surgical saw blade for precise, reproducible, and predictable wedge osteotomies.

BRIEF SUMMARY OF THE INVENTION

The apparatus of the present invention solves the problem in a simple and straightforward manner. What is provided is a surgical blade for use with a saw, the blade which includes a cutting tip, having a plurality of cutting teeth; a shaft having a cutting slope, with the plurality of teeth positioned along multiple planes on the cutting slope; a neck portion; and a saw base; wherein the saw causes the blade to oscillate as it undergoes the cutting procedure.

These and other features, aspects and advantages of the present invention will become better understood with reference to the following drawings, description and claims.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 8 illustrates a top view of an embodiment of the invention and shows the rows of cutting teeth and cutting tip having a radius.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

An embodiment of the present invention adds a slope on one side of the blade from the distal tip to the proximal shaft with teeth to allow for a precise predetermined wedge of bone to be resected with performing only one osteotomy. The present invention relates to a surgical saw blade for precise, reproducible, and predictable wedge osteotomies.

Embodiments of the present invention include a surgical saw blade for creating precise wedge osteotomies that are reproducible and predictable, to be used to correct angular deformities in bones and joints. An embodiment of the invention, which may be called a "wedge osteotomy blade," creates a precise predetermined wedge cut in bone with one pass. This can eliminate the need for two passes with a standard bone saw blade, as well as eliminate planar inconsistencies associated with multiple passes. The osteotomy is reproducible and predictable.

Figure 1:
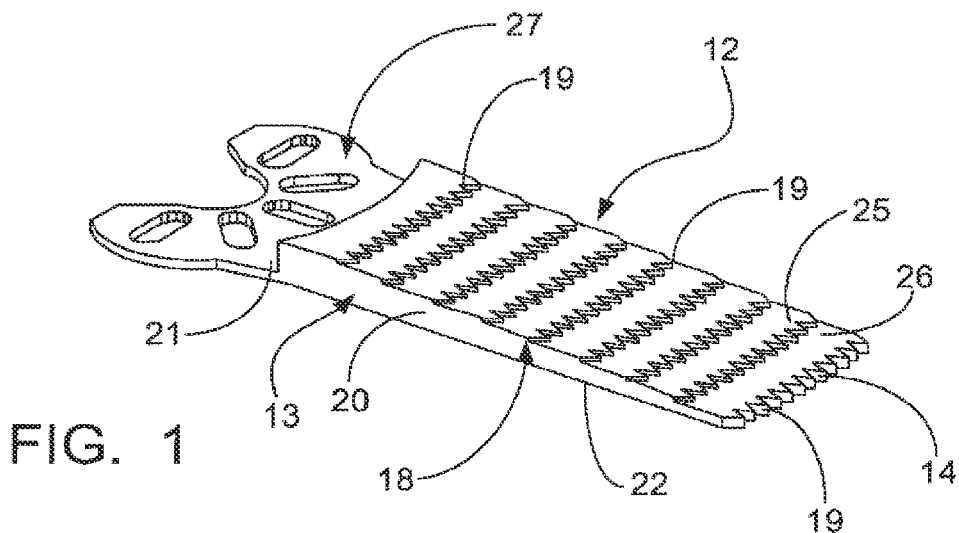
FIG. 1 illustrates an overall view of a first embodiment of the invention.
Figure 2:
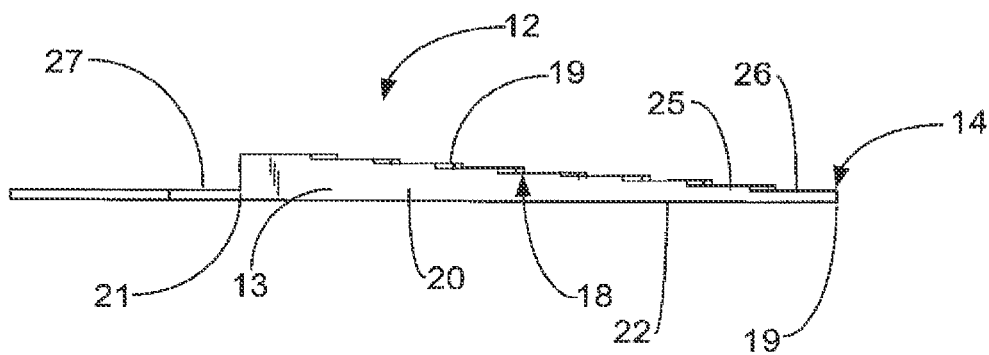
FIG. 2 illustrates a side view of a first embodiment of the invention.
Figure 3:
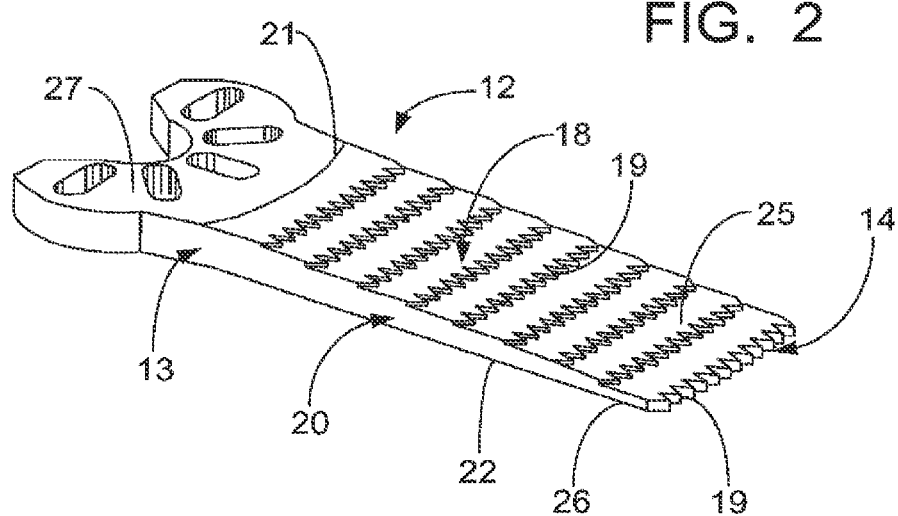
FIG. 3 illustrates an overall view of a second embodiment of the invention.
Figure 4:
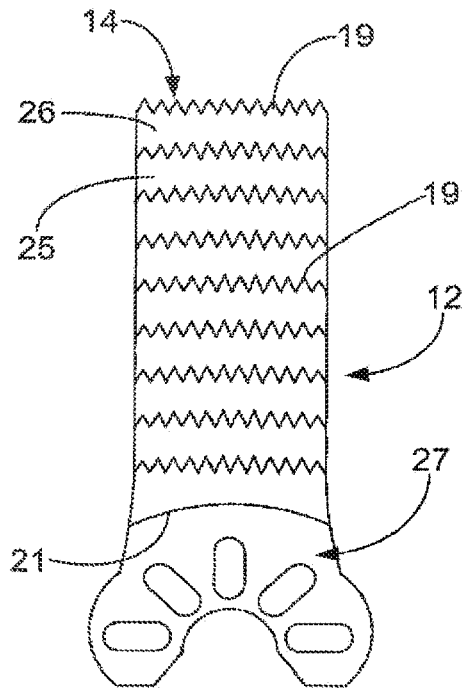
FIG. 4 illustrates a top view of a second embodiment of the invention.
Figure 7:
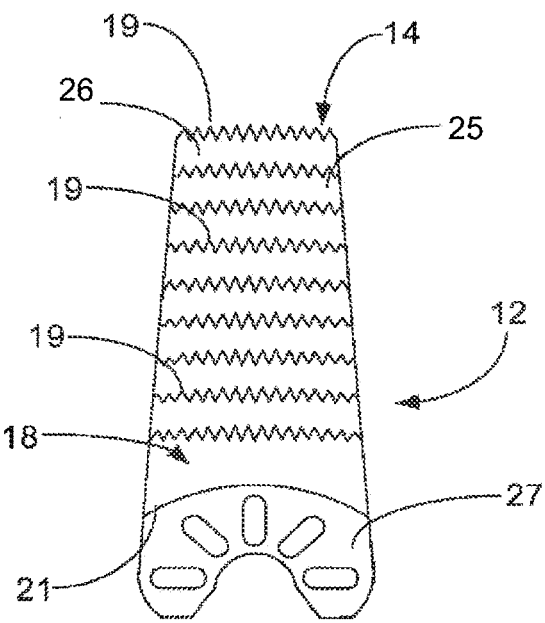
FIG. 7 illustrates a top view of a third embodiment of the invention.
Figure 5:
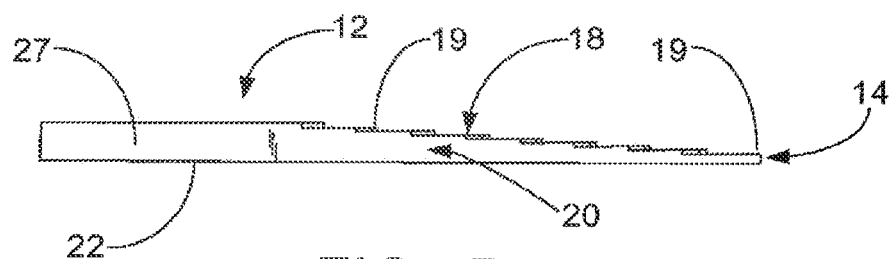
FIG. 5 illustrates a side view of a second embodiment of the invention.
Figure 6:
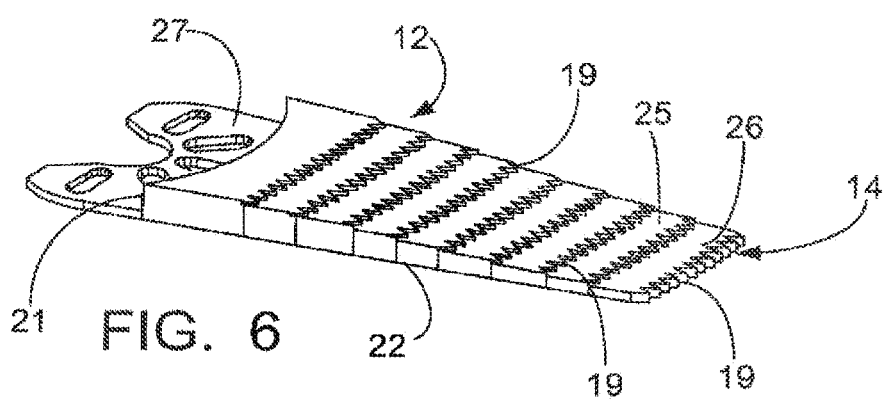
FIG. 6 illustrates an overall view of a third embodiment of the invention.

FIGS. 1 through 8 illustrate the preferred embodiments of the device of the present invention. Broadly, each embodiment of the present invention, as illustrated in FIGS. 1 through 8, is generally a surgical saw blade 12 for precise, reproducible, and predictable wedge osteotomies. Although each embodiment has slight modifications over other embodiments, it should be known that the principal inventive features as claimed are found in each embodiment as shown in the FIGS. 1 through 8.

In each embodiment, the wedge osteotomy blade 12 is a device designed to create a precise, predetermined wedge osteotomy in bone. The wedge osteotomy blade 12 could be retro-fitted to any surgical saw configuration. The wedge osteotomy blade 12 could be constructed of surgical grade stainless steel or any other material used for cutting bone that can be sterilized.

The blade 12 further comprises a blade body 13 having a cutting tip 14 which is designed with multiple teeth 19 to create a cut in bone when oscillated. This tip 14 preferably has a radius, and could contain any number of teeth. The radius R is illustrated in FIG. 8. The teeth could be any length or of any design.

There is provided a cutting slope 18 designed on one surface 25 of a shaft 20, with the underside 22 being flat. The cutting slope 18 could be any rise over run desired for creating a wedge osteotomy. The slope should be at its highest height near the neck 21 and at its lowest height at the cutting tip 14.

The cutting slope 18 has multiple rows of cutting teeth 19. Each row of teeth 19 is elevated above the run of the distal row of teeth 19. The cutting teeth 19 could be of any design and preferably have the same radius, number of teeth, and same length as the cutting tip 14.

The shaft 20 is designed to be flat on four surfaces and accommodates the cutting slope 18 on the fifth surface 25, and the cutting tip 14 on the sixth surface 26. The shaft 20 could be of any shape, preferably rectangular or trapezoidal. The shaft 20 extends from the neck 21 to the cutting tip 14. The shaft 20 could be any length and width.

The neck 21 is designed to be the transition from the shaft 20 to the saw attachment base 27.

The saw attachment base 27 allows the blade 12 to be attached to a surgical saw (not illustrated).

The invention provides the surgeon a way to make accurate wedge osteotomies with predictability and reproducibility. The wedge osteotomy blade 12 has a cutting tip 14 to start the osteotomy. The cutting slope 18 resects bone as it enters, leaving a wedge osteotomy. The cutting slope 18 has rows of cutting teeth 19 for resection of bone while oscillating. The shaft 20 is of a predetermined length and width and supports the cutting slope 18. The neck 21 is the transition of the shaft 20 into the saw attachment base 27. The saw attachment base 27 can be of any design to fit any number of surgical saw manufacturers.

The wedge osteotomy blade 12 is one component. It can be manufactured from surgical grade stainless steel or any other material used for cutting bone that can be sterilized.

The wedge osteotomy blade 12 works by creating a precise, predetermined, wedge osteotomy in bone. To perform an osteotomy with the wedge osteotomy blade 12, the Surgeon has to first attach the blade 12 to a surgical saw (not illustrated). The surgical saw could be from any manufacturer. The wedge osteotomy blade 12 which is being oscillated by the surgical saw is then introduced into the bone in a straight fashion. The surgeon can dictate whether to make a complete through and through osteotomy, or leave the distal cortex intact as a hinge. After satisfactory wedge resection, saw is disengaged and removed from bone. It leaves a precise, predetermined, wedge osteotomy for the surgeon to correct angular deformities in bones and joints.

To make this invention a detailed drawing, or a computer aided design drawing is needed. With the aforementioned drawings, one could machine a wedge osteotomy blade from surgical grade stainless steel or any other material used for cutting bone that can be sterilized.

Another way to reconfigure the wedge osteotomy blade 12 would be to have the cutting slope 18 on two opposite sides of the shaft 20 to create a two sided cutting surface for a "V" type wedge resection, instead of the "right triangle" shaped wedge.

A person would use the invention in the following way. First the saw attachment base 27 is attached to a surgical saw from any number of manufactures. The next step would be to turn the surgical saw on, which in turn would oscillate the wedge osteotomy blade 12. The surgeon then engages the bone with the cutting tip 14 first. As the surgeon advances the blade 12 in a linear fashion through the bone the cutting slope 18 resects a wedge of bone with precision, predictably, and reproducibility.

It should be understood, of course, that the foregoing relates to exemplary embodiments of the invention and that modifications may be made without departing from the spirit and scope of the invention as set forth in the following claims.

The following is a list of parts and materials suitable for use in the present invention.

| PARTS LIST | |
|---|---|
| Part Number | Description |
| 12 | wedge osteotomy blade |
| 13 | blade body |
| 14 | cutting tip |
| 18 | cutting slope |
| 19 | cutting teeth |
| 20 | shaft |
| 21 | neck |
| 22 | underside |
| 25 | fifth surface |
| 26 | sixth surface |
| 27 | saw attachment base |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A method for performing a wedge osteotomy comprising the following steps:
   a) providing a surgical blade including a blade body and a surgical tool coupler, the blade body having:
      i) a bottom,
      ii) a proximal end,
      iii) a distal end,
      iv) a cutting tip adjoining the distal end, and
      v) a cutting slope extending between the proximal end and the distal end, the cutting slope including a plurality of teeth positioned along a top surface of the cutting slope,
      wherein the bottom has a bottom plane extending to the cutting tip,
      wherein the cutting slope intersects the bottom plane,
      wherein a proximal end height of the cutting slope is higher than a distal end height of the cutting slope relative to the bottom plane, and
      wherein the surgical tool coupler adjoins the proximal end of the blade body;
   b) coupling the surgical tool coupler to a surgical tool that is able to oscillate;
   c) activating the surgical tool to cause the blade to oscillate;
   d) engaging a bone with the cutting tip of the blade along the bottom plane;

e) advancing the blade and the cutting slope forward in a linear or straight fashion to create a wedge cut in the bone with one pass of the blade.

2. The method of claim 1 wherein the plurality of teeth along the cutting slope are positioned along the cutting slope from the proximal end to the distal end.

3. The method of claim 1 wherein the plurality of teeth include a cutting edge that faces the distal end.

4. The method of claim 1 wherein at least one of the plurality of teeth is positioned along the cutting slope at a first height respective to the bottom plane and another of the plurality of teeth is positioned along the cutting slope at a second height respective to the bottom plane that is lower than the first height.

5. The method of claim 1 wherein the plurality of cutting teeth along the cutting slope are positioned in offset planes along the cutting slope.

6. The method of claim 1, wherein the cutting slope is a first cutting slope and the surgical blade further comprises a second cutting slope on an opposite side of the bottom plane from the first cutting slope.

7. The method of claim 6 wherein in step "e" advancing the blade resects a "V" shaped wedge cut in the bone.

8. A method for performing a wedge osteotomy comprising the following steps:
   a) providing a surgical blade having a wedge shape, the surgical blade having a blade body comprising:
   i) a slope including a first plurality of teeth along the slope;
   ii) a bottom including a bottom plane;
   iii) a proximal end;
   iv) a distal end; and
   v) a cutting tip in line with the bottom plane and including a cutting tip edge that is distally facing, wherein the cutting tip is positioned at the distal end and wherein the slope ends at the cutting tip;
   b) coupling the surgical blade to a surgical instrument;
   c) activating the surgical instrument;
   d) engaging a bone with the cutting tip of the surgical blade; and
   e) advancing the surgical blade in a forward direction along the bottom plane to resect a wedge-shaped cut in the bone with one pass of the blade.

9. The method of claim 8 wherein the first plurality of teeth are positioned along the slope from the proximal end to the distal end of the blade body.

10. The method of claim 8 wherein the first plurality of teeth have a cutting surface that is distally facing.

11. The method of claim 8 wherein at least one of the first plurality of teeth is positioned along the slope at a first height respective to the bottom plane and another of the plurality of teeth is positioned along the slope at a second height respective to the bottom plane that is lower than the first height.

12. A method for performing an osteotomy comprising the following steps:
   a) providing a blade having a proximal end and a distal end, the blade comprising:
   i) an attachment base positioned at the proximal end; and
   ii) a blade body including exterior surfaces, wherein:
   a first exterior surface includes a cutting tip having a first plurality of cutting teeth along the distal end for starting the osteotomy,
   a second exterior surface opposite the first exterior surface and which transitions to the attachment base,
   a third exterior surface that is a top surface and extends between the first exterior surface and the second exterior surface, that is sloped, and that includes a second plurality of teeth,
   a fourth exterior surface opposite the third exterior surface that is a bottom surface with a bottom plane extending to the cutting tip,
   a fifth exterior surface extending between the first exterior surface and the second exterior surface, and
   a sixth exterior surface opposite the fifth exterior surface;
   b) coupling the attachment base to a surgical instrument;
   c) activating the surgical instrument;
   d) engaging a bone with the cutting tip; and
   e) advancing the blade body forward in straight fashion along the bottom plane to resect a wedge-shape cut in the bone in one pass of the blade.

13. The method of claim 12 wherein the second plurality of teeth along the third exterior surface are positioned from the proximal end to the distal end.

14. The method of claim 12 wherein the second plurality of teeth include a cutting edge that faces the distal end.

15. The method of claim 12 wherein at least one of the second plurality of teeth is positioned along the third exterior surface at a first height respective to the bottom plane and another of the plurality of teeth is positioned along the third exterior surface at a second height respective to the bottom plane that is lower than the first height.

16. The method of claim 12 wherein the second plurality of teeth along the third exterior surface are positioned in offset planes.

17. The method of claim 12, wherein the fourth exterior surface includes a sloped portion that includes a third plurality of teeth, wherein the sloped portion is on an opposite side of the bottom plane from the third exterior surface.

18. The method of claim 17 wherein in step "e" the wedge-shape cut in the bone has a "V" shape.

\* \* \* \* \*